United States Patent
Nekrassov et al.

(10) Patent No.: US 12,207,874 B2
(45) Date of Patent: Jan. 28, 2025

(54) EVALUATING MEASUREMENTS USING INFORMATION FROM MULTIPLE MEASURING DEVICES

(71) Applicant: Alcon Inc., Fribourg (CH)

(72) Inventors: Daniil Nekrassov, Berlin (DE); George Hunter Pettit, Fort Worth, TX (US); Martin Gründig, Rangsdorf (DE); Mark Andrew Zielke, Lake Forest, CA (US); John Alfred Campin, Southlake, TX (US)

(73) Assignee: Alcon Inc., Fribourg (CH)

( * ) Notice: Subject to any disclaimer, the term of this patent is extended or adjusted under 35 U.S.C. 154(b) by 591 days.

(21) Appl. No.: 17/574,686

(22) Filed: Jan. 13, 2022

(65) Prior Publication Data

US 2022/0225874 A1    Jul. 21, 2022

Related U.S. Application Data

(60) Provisional application No. 63/139,581, filed on Jan. 20, 2021.

(51) Int. Cl.
*A61B 3/00* (2006.01)
*A61B 3/10* (2006.01)
(Continued)

(52) U.S. Cl.
CPC ............ *A61B 3/107* (2013.01); *A61B 3/0025* (2013.01); *A61B 3/102* (2013.01)

(58) Field of Classification Search
CPC ..... A61B 3/0025; A61B 3/1015; A61B 3/102; A61B 3/103; A61B 3/107; A61B 3/1173;
(Continued)

(56) References Cited

U.S. PATENT DOCUMENTS

| | | |
|---|---|---|
| 2015/0077705 A1 | 3/2015 | Artsyukhovich et al. |
| 2017/0027437 A1 | 2/2017 | Neal et al. |
| 2018/0242840 A1 | 8/2018 | Copland |

FOREIGN PATENT DOCUMENTS

| | | |
|---|---|---|
| WO | 2016089395 A1 | 6/2016 |
| WO | 2017019117 A1 | 2/2017 |

OTHER PUBLICATIONS

Mehdi Bahrami et al, "Geometry-invariant gradient refractive index lens: analytical ray tracing", Journal of Biomedical Optics, May 2012;17:055001.

(Continued)

*Primary Examiner* — Jack Dinh

(57) ABSTRACT

An ophthalmic system for measuring an eye comprises measuring devices and a computer. The measuring devices comprise an optical coherence tomography (OCT) device and an aberrometer. The OCT device directs OCT light towards the eye, and detects the OCT light reflected from the eye to measure the eye. The aberrometer directs aberrometer light towards the eye, and detects the aberrometer light reflected from the eye to measure the eye. The computer generates an ocular model of the eye according to the reflected OCT light. The ocular model comprises parameters for the eye, where each parameter is assigned a value. The computer determines an OCT-based wavefront according to the ocular model, determines an aberrometer-based wavefront according to the reflected aberrometer light, ascertains a deviation between the OCT-based wavefront and the aberrometer-based wavefront, and evaluates measurements from one or more of the measuring devices according to the deviation.

20 Claims, 6 Drawing Sheets

(51) Int. Cl.
  *A61B 3/103* (2006.01)
  *A61B 3/107* (2006.01)
  *A61B 3/117* (2006.01)
  *G06T 15/06* (2011.01)

(58) Field of Classification Search
  CPC ........ G16H 40/63; G16H 50/20; G16H 50/30;
    G16H 50/50; G06T 15/06; G06T 2210/41
  See application file for complete search history.

(56) References Cited

OTHER PUBLICATIONS

Navarro et al., "Adaptive model of the gradient index of thehuman lens. II. Optics of the accommodating aging lens", Journal of the Optical Society of America A: Optometry, Image Science & Vision, 2007; 24:2911-2920.
Patel et al, "The refractive index of the human cornea: A review", Contact Lens and Anterior Eye 42 (2019) 575-580.
Sheil et al, "Crystalline lens paradoxes revisited: significance of age-related restructuring of the GRIN", Biomedical Optics Express, Sep. 1, 2017; 8:4172-4180.

EVALUATING MEASUREMENTS USING INFORMATION FROM MULTIPLE MEASURING DEVICES

TECHNICAL FIELD

The present disclosure relates generally to ophthalmic measuring devices, and more particularly to evaluating measurements using information from multiple measuring devices.

BACKGROUND

Ophthalmic measuring systems typically address a particular application. For example, a dedicated system provides measurements for calculating an intraocular lens (IOL) power for a cataract surgery. The systems generally do not have multiple devices that provide measurements for the same thing. Accordingly, measurement errors can be difficult to detect. Some doctors use measurements from multiple systems to check for errors or average the output from multiple systems to obtain a measurement. Such approaches are time-consuming and often ineffective at obtaining accurate measurements.

BRIEF SUMMARY

In certain embodiments, an ophthalmic system for measuring an eye comprises measuring devices and a computer. The measuring devices comprise an optical coherence tomography (OCT) device and an aberrometer. The OCT device directs OCT light towards the eye, and detects the OCT light reflected from the eye to measure the eye. The aberrometer directs aberrometer light towards the eye, and detects the aberrometer light reflected from the eye to measure the eye. The computer generates an ocular model of the eye according to the reflected OCT light. The ocular model comprises parameters for the eye, where each parameter is assigned a value. The computer determines an OCT-based wavefront according to the ocular model, determines an aberrometer-based wavefront according to the reflected aberrometer light, ascertains a deviation between the OCT-based wavefront and the aberrometer-based wavefront, and evaluates measurements from one or more of the measuring devices according to the deviation.

Embodiments may have none, one, some, or all of the following features: The computer evaluates measurements by identifying one or more problems related to the deviation. The one or more problems may be associated with a measurement condition or a measuring device. The one or more problems may be a tear film instability, an inaccurate lens topography parameter, an inadequate patient fixation, an inadequate device alignment, and/or an inadequate device calibration.

The computer evaluates measurements by identifying one or more measuring devices associated with the deviation.

The measuring devices comprise a topographer that directs topographer light towards the eye, and detects the topographer light reflected from the eye. The computer generates the ocular model of the eye by: determining an OCT-based anterior corneal surface from the ocular model, determining a topographer-based anterior corneal surface from the reflected topographer light, and checking the ocular model by comparing the OCT-based anterior corneal surface and the topographer-based anterior corneal surface. The computer may evaluate one or more measurements by: identifying one or more related problems comprising a problem selected from a group consisting of an insufficient sampling, a tear film instability, an inadequate device alignment, and an inadequate device calibration.

The computer ascertains the deviation between the OCT-based wavefront and the aberrometer-based wavefront by: calculating OCT-based sphere and cylinder parameters of a simulated wavefront through the ocular model, calculating aberrometer-based sphere and cylinder parameters of the aberrometer-based wavefront, and comparing the OCT-based sphere and cylinder parameters and the aberrometer-based sphere and cylinder parameters. The computer may evaluate one or more measurements by: identifying one or more related problems comprising an inaccurate axial length measurement, an inadequate patient fixation, an inadequate device alignment, and/or an inadequate device calibration.

The computer ascertains the deviation between the OCT-based wavefront and the aberrometer-based wavefront by: determining one or more aberrometer-based values of the aberrometer-based wavefront, determining one or more OCT-based values of the ocular model, and comparing the one or more aberrometer-based values and the OCT-based values. The one or more aberrometer-based values may comprise one or more aberrometer-based slopes of the aberrometer-based wavefront. The one or more OCT-based values may comprise one or more OCT-based slopes of one or more rays exiting the ocular model.

The computer adjusts one or more values assigned to one or more of the parameters by repeating the following until an adjusted OCT-based wavefront and the aberrometer-based wavefront satisfies a predefined tolerance: adjusting the one or more values to yield an adjusted ocular model, determining the adjusted OCT-based wavefront according to the adjusted ocular model, and comparing the adjusted OCT-based wavefront and the aberrometer-based wavefront to check if they satisfy the predefined tolerance.

The OCT device checks the ocular model by: directing next OCT light towards the eye at an angle different from an angle of the OCT light, and detecting the next OCT light reflected from the eye. The aberrometer checks the ocular model by: directing next aberrometer light towards the eye at an angle different from an angle of the aberrometer light, and detecting the next aberrometer light reflected from the eye. The computer checks the ocular model by: generating a next ocular model of the eye according to the reflected next OCT light, generating a next aberrometer-based wavefront according to the reflected next aberrometer light, determining a next OCT-based wavefront according to the next ocular model, and comparing the next OCT-based wavefront and the next aberrometer-based wavefront.

In certain embodiments, an ophthalmic system for measuring an eye comprises measuring devices and a computer. The measuring devices comprise an optical coherence tomography (OCT) device and a topographer. The OCT device directs OCT light towards the eye, and detects the OCT light reflected from the eye. The topographer directs topographer light towards the eye, and detects the topographer light reflected from the eye. The computer determines an OCT-based anterior corneal surface from the reflected OCT light, determines a topographer-based anterior corneal surface from the reflected topographer light, ascertains a deviation between the OCT-based anterior corneal surface and topographer-based anterior corneal surface, and evaluates the OCT-based anterior corneal surface and the topographer-based anterior corneal surface according to the deviation.

Embodiments may have none, one, some, or all of the following features: The computer evaluates the OCT-based anterior corneal surface and the topographer-based anterior corneal surface by identifying one or more problems related to the deviation. The one or more related problems may be associated with a measurement condition or a measuring device. The one or more related problems may comprise an insufficient sampling, an inadequate device alignment, and/or an inadequate device calibration.

The computer evaluates the OCT-based anterior corneal surface and the topographer-based anterior corneal surface by identifying one or more measuring devices associated with the deviation.

The measuring devices comprise an aberrometer that directs aberrometer light towards the eye, and detects the aberrometer light reflected from the eye. The computer generates an ocular model of the eye according to the reflected OCT light. The ocular model comprises parameters for the eye, where each parameter is assigned a value. The computer determines an OCT-based wavefront according to the ocular model, determines an aberrometer-based wavefront according to the reflected aberrometer light, compares the OCT-based wavefront and the aberrometer-based wavefront, and evaluates one or more measurements from one or more of the plurality of measuring devices according to the comparison.

In certain embodiments, an ophthalmic system for measuring an eye comprises measuring devices and a computer. The measuring devices comprise an optical coherence tomography (OCT) device, an aberrometer, and a topographer. The OCT device directs OCT light towards the eye, and detects the OCT light reflected from the eye to measure the eye. The aberrometer directs aberrometer light towards the eye, and detects the aberrometer light reflected from the eye to measure the eye. The topographer directs topographer light towards the eye, and detects the topographer light reflected from the eye. The computer generates an ocular model of the eye according to the reflected OCT light. The ocular model comprises parameters for the eye, where each parameter is assigned a value. The ocular model is generated by: determining an OCT-based anterior corneal surface from the ocular model, determining a topographer-based anterior corneal surface from the reflected topographer light, and checking the ocular model by comparing the OCT-based anterior corneal surface and the topographer-based anterior corneal surface. The computer determines an OCT-based wavefront according to the ocular model, determines an aberrometer-based wavefront according to the reflected aberrometer light, and ascertains a deviation between the OCT-based wavefront and the aberrometer-based wavefront. The deviation between the OCT-based wavefront and the aberrometer-based wavefront is ascertained by: calculating OCT-based sphere and cylinder parameters of a simulated wavefront through the ocular model, calculating aberrometer-based sphere and cylinder parameters of the aberrometer-based wavefront, and comparing the OCT-based sphere and cylinder parameters and the aberrometer-based sphere and cylinder parameters; and determining one or more aberrometer-based values of the aberrometer-based wavefront, determining one or more OCT-based values of the ocular model, and comparing the one or more aberrometer-based values and the OCT-based values, wherein the one or more aberrometer-based values comprise one or more aberrometer-based slopes of the aberrometer-based wavefront, and the one or more OCT-based values comprise one or more OCT-based slopes of one or more rays exiting the ocular model. The computer evaluates one or more measurements from one or more of the measuring devices according to the deviation by: identifying one or more problems related to the deviation and associated with a measurement condition or a measuring device, the one or more related problems comprising a problem selected from a group consisting of an inaccurate axial length measurement, an insufficient sampling, a tear film instability, an inaccurate lens topography parameter, an inadequate patient fixation, an inadequate device alignment, and an inadequate device calibration; and identifying one or more measuring devices associated with the deviation. The computer adjusts one or more values assigned to one or more of the parameters by repeating the following until an adjusted OCT-based wavefront and the aberrometer-based wavefront satisfies a predefined tolerance: adjusting the one or more values to yield an adjusted ocular model, determining the adjusted OCT-based wavefront according to the adjusted ocular model, and comparing the adjusted OCT-based wavefront and the aberrometer-based wavefront to check if they satisfy the predefined tolerance. The OCT device checks the ocular model by: directing next OCT light towards the eye at an angle different from an angle of the OCT light, and detecting the next OCT light reflected from the eye. The aberrometer checks the ocular model by: directing next aberrometer light towards the eye at an angle different from an angle of the aberrometer light, and detecting the next aberrometer light reflected from the eye. The computer checks the ocular model by: generating a next ocular model of the eye according to the reflected next OCT light, generating a next aberrometer-based wavefront according to the reflected next aberrometer light, determining a next OCT-based wavefront according to the next ocular model, and comparing the next OCT-based wavefront and the next aberrometer-based wavefront.

DESCRIPTION OF EXAMPLE EMBODIMENTS

Figure 1:
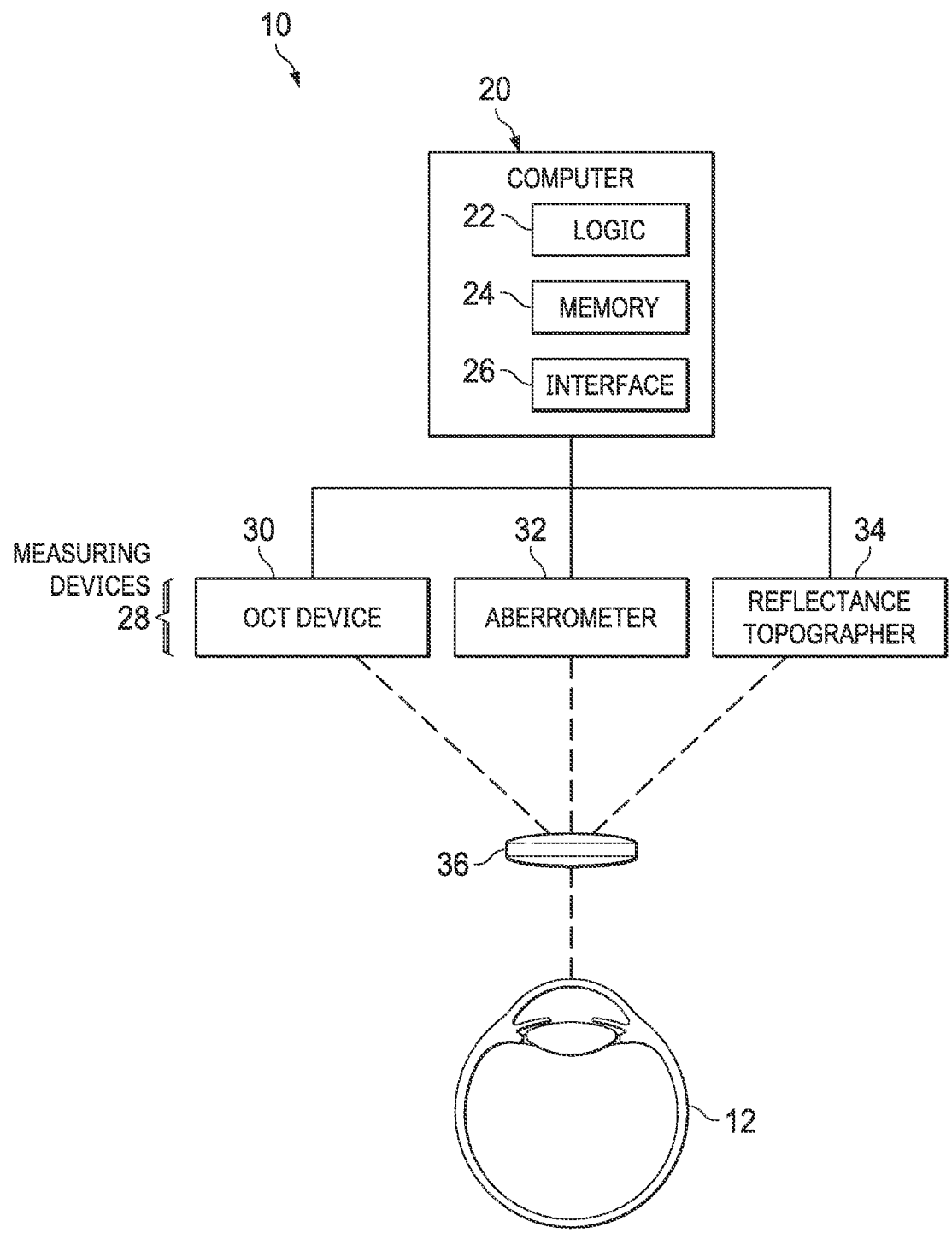
FIG. 1 illustrates an example of a system that evaluates measurements of an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Embodiments of the disclosed systems and methods evaluate measurements from a measuring device by comparing them with measurements from another device. In certain embodiments, the measurements are compared by comparing wavefronts derived from the measurements.

FIG. 1 illustrates an example of a system 10 that evaluates measurements of an eye 12, according to certain embodiments. In the example, system 10 includes a computer 20 (which includes logic 22, a memory 24, and an interface 26), measuring devices 28, and an optical system 36, coupled as shown. Measuring devices 28 include an optical coherence tomography (OCT) device 30, an aberrometer 32, and a topographer 34, coupled as shown.

According to an example of operation, computer 20 generates an ocular model of eye 12 according to measurements from OCT device 30. Computer 20 determines an OCT-based wavefront from the ocular model and an aberrometer-based wavefront from aberrometer 32. Computer 20 compares the OCT-based and aberrometer-based wavefronts. If there is a deviation, the computer evaluates measurements according to the deviation.

Turning to the parts of system 10, measuring devices 28 include OCT device 30, aberrometer 32, and topographer 34. OCT device 30 directs OCT light towards eye 12 and detects the OCT light reflected from parts of eye 12 to generate an image of the parts. OCT device 30 may be any suitable device that uses OCT to capture two- or three-dimensional images from within optical scattering media, e.g., eye tissue. OCT device 30 may use time domain, frequency domain, or other suitable spectral encoding, and may use single point, parallel, or other suitable scanning. An example of operation is described in more detail with reference to FIG. 2.

Figure 2:
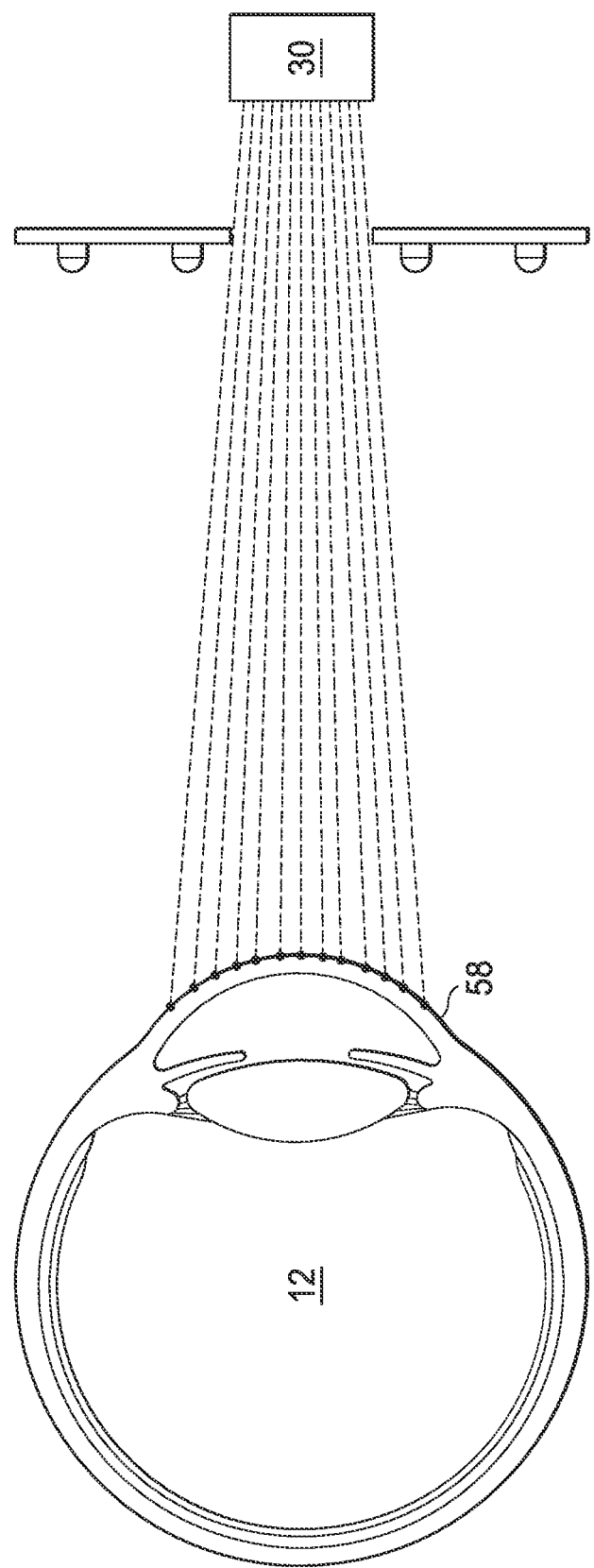
FIG. 2 illustrates an example of an OCT device measuring the anterior corneal surface of an eye.

FIG. 2 illustrates an example of OCT device 30 measuring the anterior corneal surface 58 of eye 12. In general, OCT device 30 detects reflections of light from an interface between media, e.g., between the air and eye 12 or between parts of eye 12, such as between the cornea and aqueous humor. OCT device 30 records the optical path length of the detected light and converts the optical path lengths to physical distances. In certain embodiments, raw data from OCT device 30 is converted such that the distances to the interfaces of eye 12 is expressed "as in air", i.e., not taking into account the refractive indices of the tissue.

In the illustrated example, OCT device 30 detects reflections of light from anterior corneal surface 58, records the optical path length of the detected light, and expresses the distance to anterior corneal surface 58 "as in air". The distances to different points of surface 58 can be used to construct surface 58 in an ocular model. OCT device 30 measures the distances to the interfaces between other parts of eye 12 in a similar manner to construct the rest of the ocular model.

Returning to FIG. 1, aberrometer 32 directs aberrometer light towards eye 12 and detects the aberrometer light reflected from eye 12. Aberrometer 32 uses aberrometry (i.e., wavefront technology) to measure how light travels through eye 12 to retina, which reflects the light. An aberration of the eye causes the light to take on a different shape, which can be used to characterize the aberration. Aberrometer 32 generates a wavefront map (e.g., a Zernike coefficient map) from the reflected light. A Hartmann-Shack aberrometer is an example of an aberrometer 32.

Reflection topographer 34 directs topographer light towards the eye, and detects the topographer light reflected from the eye to measure the shape of anterior corneal surface 58. In certain embodiments, measurements from topographer 34 and OCT device 30 are used to construct anterior corneal surface 58 of the ocular model. An example of operation is described in more detail with reference to FIG. 3.

Figure 3:
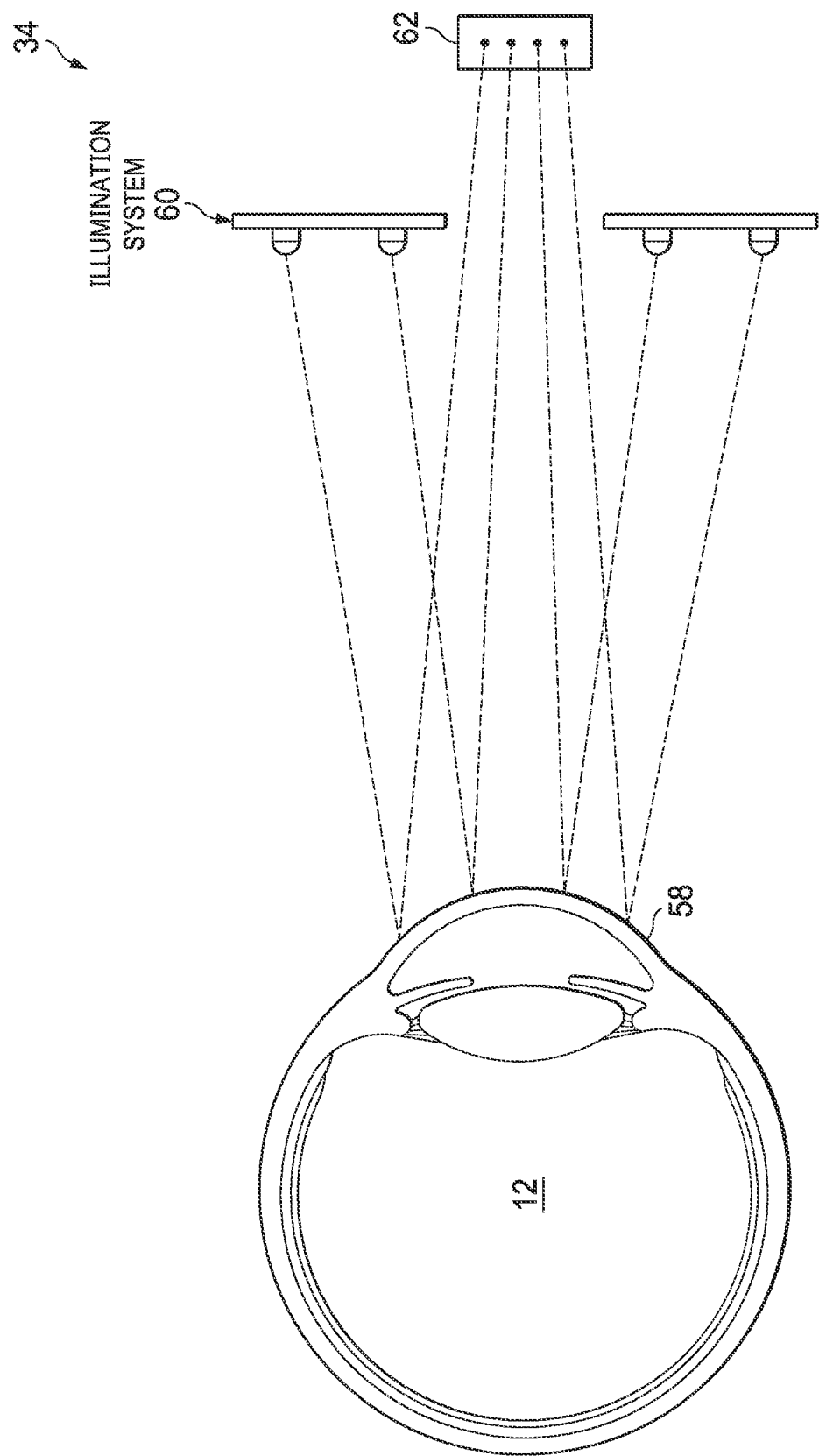
FIG. 3 illustrates an example of a topographer measuring the anterior corneal surface of an eye.

FIG. 3 illustrates an example of a topographer 34, such as a reflection topographer, measuring the anterior corneal surface of eye 12. In the example, topographer 34 includes an illumination system 60 and a sensor 62. Illumination system 60 directs topographer light towards the eye. The light projects a pattern (e.g., concentric rings or grid of dots) onto anterior corneal surface 58. Sensor 62 (e.g., a camera) detects the topographer light reflected from the eye and generates an image of the reflected light. The image is analyzed to determine features of the eye, e.g., the shape of surface 58. If the surface is an ideal sphere, the reflected pattern matches the projected pattern. If the surface has aberrations, areas where the reflected portions of the pattern (e.g. rings or dots) are closer together may indicate steeper corneal curvature, and areas where the portions are farther part may indicate flatter areas. Topographer 34 may output the results in the form of a map of the surface, such as an axial, tangential, refractive power, or elevation map.

Returning to FIG. 1, measuring devices 28 may acquire measurements sequentially and/or simultaneously. To compare the measurements, the measurements should be aligned. In certain cases, the measurements may be aligned using a feature of eye 12, e.g., the pupil or iris markings. In other cases, the measurements may be aligned using eye-tracking functions. In other cases, measuring devices 28 may take measurements along the same optical path such that eye 12 has the same alignment for the measurements. An example of measuring devices 28 making measurements along the same optical path is described with reference to FIG. 4.

Figure 4:
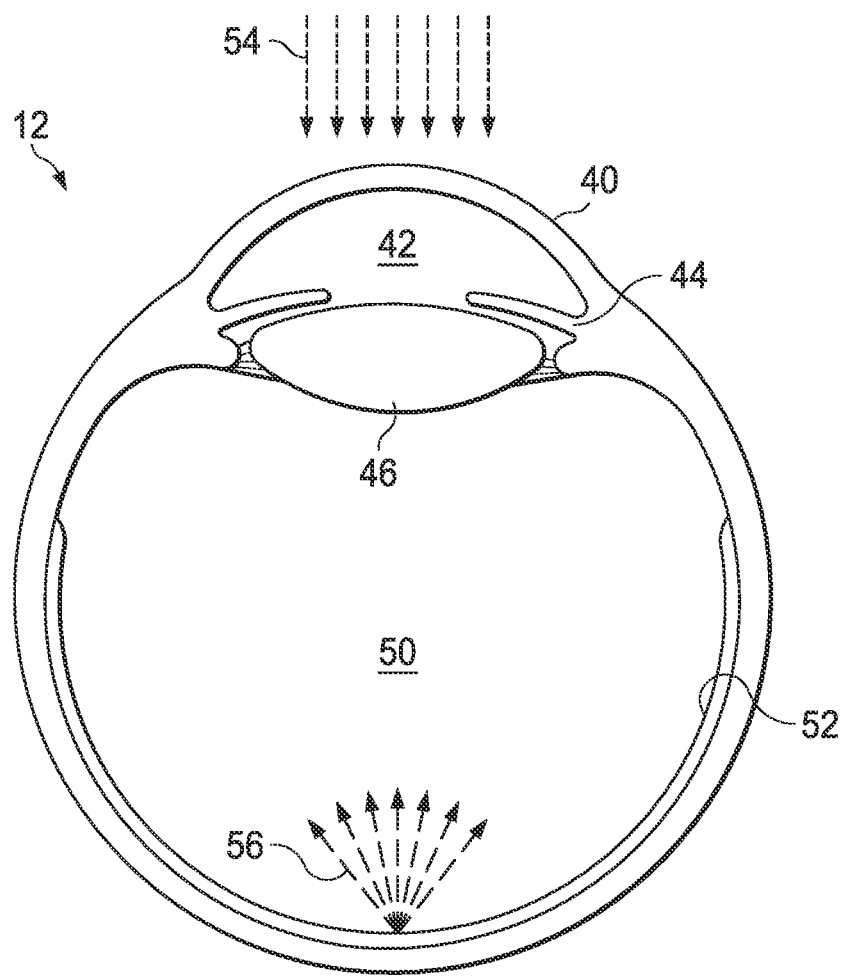
FIG. 4 illustrates an example of OCT light and aberrometer light interacting with an eye.

FIG. 4 illustrates an example of OCT light 54 and aberrometer light 56 interacting with eye 12. In the example, eye 12 includes ocular parts, e.g., a cornea 40, aqueous humor 42, an iris 44, a lens 46, vitreous humor 50, and a retina 52. In certain embodiments, one or more surfaces of and/or the interfaces between parts of eye 12 may be regarded as anatomical interfaces that may be used to generate an ocular model. For example, anatomical interfaces may include: the anterior surface of cornea 40; interfaces between cornea 40, aqueous humor 42, iris 44, lens 46, vitreous humor 50, and/or retina 52; and retina 52.

In the example, OCT beams 54 enter the cornea 40, and aberrometer rays 56 reflect from retina 52. If eye 12 is an ideal emmetrope (with no optical aberrations), then each OCT ray 54 has a reflecting wavefront ray 56 traveling exactly the same optical path, just in reverse. If eye 12 has optical aberrations, the aberrations cause rays 54, 56 from the measurement devices 28 to travel different paths through eye 12. In the illustrated example, OCT beams 54 are parallel. However, OCT beams 54 may have any other suitable beam geometry, e.g., a single scanning OCT beam. As long as the beam geometry is known, the paths of OCT beams 54 can be determined.

Returning to FIG. 1, optical system 36 includes one or more optical elements that direct light from measuring devices 28 towards eye 12. An optical element can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM).

Computer 20 controls the operation of system 10 to evaluate measurements from measuring devices 28. In certain embodiments, computer 20 generates an ocular model of eye 12 according to measurements from OCT device 30. Computer 20 determines an OCT-based wavefront from the ocular model and an aberrometer-based wavefront from aberrometer 32. Computer 20 compares the OCT-based and aberrometer-based wavefronts. If there is a deviation the computer evaluates measurements according to the deviation. In certain embodiments, computer 20 may perform additional checks on the model.

Generating an Ocular Model: Ocular Models. An ocular model may comprise parameters that describe eye 12, where each parameter is assigned a value. A parameter may describe a characteristic (e.g., location, dimension, shape, and/or material property such as refractive index) of a feature (e.g., a part such as the cornea of lens) of eye 12. Parameters may describe, e.g., the following of eye 12 or a part of eye 12: (1) wavefront of eye 12; (2) shape of a surface of a part of eye 12 (e.g., anterior or posterior corneal or lens surface); (3) distance (e.g., physical or optical) through or between parts of eye 12 (e.g., between posterior cornea and anterior lens, between posterior lens and retina, or through cornea, lens, vitreous, or aqueous humor); and refractive index of a part of eye 12. The value assigned to a parameter gives the specific value for the parameter, e.g., the specific thickness of the cornea.

Parameter values are subject to constraints. Constraints can be harder constraints that have a higher priority to be satisfied, or softer constraints with a lower priority to be satisfied. In certain examples, the following parameter values may be certain and be considered harder constraints: (1) whole eye: wavefront; (2) cornea: shape of anterior and posterior surfaces, physical and optical distance through, and refractive index; (3) aqueous humor: physical distance through and refractive index; (4) lens: shape of anterior lens surface, optical path length through, and general refractive index profile (but without specific values); (5) vitreous: physical distance through and refractive index. In the examples, the following parameter values may be uncertain and be considered variables or softer constraints: (1) lens: shape of posterior lens surface, physical path through, and specific values of refractive index profile; (2) vitreous: beam direction through; (3) retina: location, shape of surface.

Generating an Ocular Model: Ray-Tracing. Computer 20 may generate the ocular model according to reflected OCT light in any suitable manner. In certain embodiments, computer 20 applies a ray-tracing procedure to generate the ocular model. Ray-tracing determines the paths of rays through eye 12, including how interfaces between parts of eye 12 refract the ray. At tissue boundaries, refraction is calculated according to according to Snell's Law, which states the ratio of the sines of the angles θ of incidence and refraction is equivalent to the reciprocal of the ratio of the indices of refraction n: $\sin \theta_2 / \sin \theta_1 = n_1/n_2$. A ray traveling through a part of eye 12 with a uniform refractive index propagates in a constant direction, while a ray traveling in a part with a gradient refractive index travels in a curved path. As the rays travel through eye 12, the process calculates the intersections between rays and surfaces, as well as the surface normals at those points, to determine the new direction of the ray according to Snell's Law. The points and surface normals at the points can be used to determine the shape of a surface. An example of such process is described with reference to FIGS. 5A and 5B.

Figure 5A:
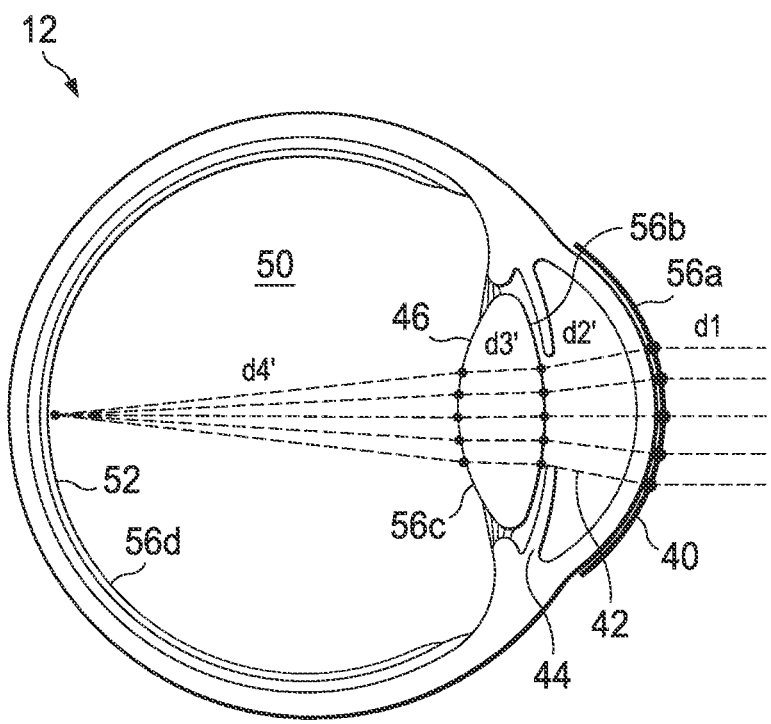
FIGS. 5A and 5B illustrate an example of applying a ray-tracing procedure to determine the locations of the anatomical interfaces of an eye in order to generate an ocular model.
Figure 5B:
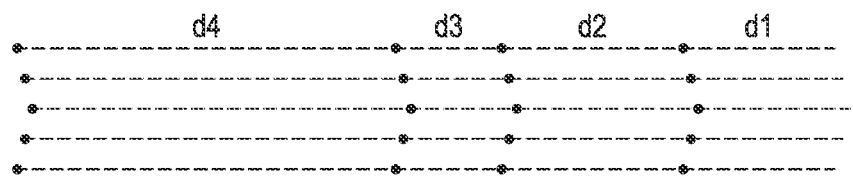

FIGS. 5A and 5B illustrate an example of applying a ray-tracing procedure to determine the locations of the anatomical interfaces 56 of eye 12 in order to generate an ocular model. FIG. 5A illustrates anatomical interfaces 56, which include: interface 56a (anterior corneal surface 58); interface 56b between aqueous humor 42 and lens 46 (anterior lens surface); interface 56c between lens 46 and vitreous humor 50 (posterior lens surface); and interface 56d (surface of retina 52). Distance d' represents the physical distance to an interface 56.

FIG. 5B illustrates measurements from OCT device 30, which records the distances d an OCT ray travels to a point of interfaces 56 as measured "as in air". The ray travels through air to interface 56a, so distance $d_1 = d'_1$. However, the ray travels through eye tissue to interfaces 56b to 56d, which decreases the distance, such that $d'_i < d_i$, where i=b, c, and d.

According to an example of operation, computer 20 defines rays traveling through the anatomical interfaces of eye 12, determines the locations of the anatomical interfaces from the rays, and generates the ocular model using the locations of the anatomical interfaces. Computer 20 defines a ray by repeating the following for each anatomical interface: determine the angle of refraction from an anatomical interface using the refractive indices of the tissue and angle of incidence; and determine the distance to the next anatomical interface from the OCT measurements.

In the example, OCT device 30 provides initial "in air" distances d to points of interfaces 56. In certain embodiments, topographer 34 may provide additional measurements for the shape of interface 56a (anterior corneal surface 58). In addition, uncertain parameter values may be assigned initial values that may be adjusted in response to additional information. For example, anterior corneal surface 58 may be initially parameterized, e.g., expressed in terms of parameters with initial values assigned to the parameters. The initial values may be, e.g., average values for a population.

Starting from interface 56a (anterior corneal surface 58), OCT device 30 provides distances $d_1 = d'_1$ to points of interface 56a. Distances $d'_2$ to points of interface 56b (anterior lens surface) may be calculated from the distances $d_2$ to the points and the refractive index of the aqueous humor. The angle of refraction at the points of interface 56b may be calculated from the shape of the anterior lens surface, direction of the ray, aqueous humor refractive index, and lens refractive index at the points. Distances d' to points of the remaining interfaces 56d and 56d may be calculated in a similar matter.

Computer 20 constructs the ocular model from the lengths and positions of the rays. The points where rays intersect interfaces 56 and surface normals at the points can be used to determine the shape of interfaces 56. In certain embodiments, computer 20 constructs the ocular model by modifying an existing model. In other embodiments, computer 20 constructs the ocular model from the raw data.

In certain cases, computer 20 may take into account additional aspects of eye 12 while generating the eye model. These additional aspects may be found, e.g., in the medical history of eye 12. Examples of such considerations include the refractive index of the IOL of a pseudophakic patient, an atypical corneal refractive index of a previously cross-linked cornea, and an atypical corneal surface of a keratoconic cornea.

Generating an Ocular Model: Checking the Model. In certain embodiments, computer 20 may check the ocular model by comparing one or more parameter values of the ocular model to values of other measurements of eye 12, e.g., measurements from measuring devices 28 of system 10 or external to system 10. A significant deviation among values may indicate a problem. A significant deviation may be, e.g., a deviation outside of one or two standard deviations or greater than a specified percentage such as 2% or 5%. Examples of problems include a problem with: the measurement conditions (e.g., insufficient sampling, inadequate patient fixation, and/or tear film instability), the measuring device 28 (e.g. device alignment and/or calibration), or the parameters of the model (e.g., corneal parameters). In some cases, a deviation may have a particular signature that indicates the likely problem.

Computer 20 may respond to detecting the deviation in any suitable manner. For example, computer 20 may send a notification identifying one or more related problems, e.g., one or more problems responsible for or likely responsible for the deviation. As another example, computer 20 may provide a recommendation to redo the measurements with one or more measuring devices 28 associated with the deviation, e.g., that could be responsible for the deviation. As another example, computer 20 may identify conditions of eye 12 (e.g., from the medical history of eye 12) that provides context for the deviation and notify the user of the conditions.

Comparing Anterior Corneal Surfaces. In certain embodiments, computer 20 may compare values describing anterior corneal surface 58 of the ocular model with values from other descriptions of anterior corneal surface 58, e.g., measurements of toric power or anterior corneal surface 58 as measured by topographer 34. A significant deviation may indicate a problem with, e.g., insufficient sampling of surface 58 and/or inadequate device issue (e.g., inadequate device alignment or calibration). For example, computer 20 may determine that the measurements of surface 58 from OCT device 30 and/or topographer 34 are insufficient, or that the measurements of OCT device 30 and/or topographer are not aligned with other measurements. Computer 20 may send a notification identifying the problem or likely problems and/or a recommendation to redo the measurements with one or more measuring devices 28 (e.g., OCT device 30 and/or topographer 34) that could be responsible for the deviation.

Determining Wavefronts. Ocular wavefronts are typically measured at the corneal surfaces or entrance pupil plane of the eye. However, the wavefront may be calculated (using aberrometry and/or anatomic OCT data) at any suitable location, e.g., the anterior lens surface. Computer 20 may determine an OCT-based wavefront according to the ocular model in any suitable manner. In certain embodiments, computer 20 determines the OCT-based wavefront by applying a ray-tracing procedure to the ocular model. Rays originating from a spot on the retina are propagated through eye 12, similar to what is shown in FIG. 5A, but in the reverse direction. Computer 20 obtains the position and orientation of the rays at the selected location, and constructs the OCT-based wavefront from the position and orientation. Computer 20 determines the aberrometer-based wavefront according to the reflected aberrometer light from aberrometer 32. In certain embodiments, aberrometer 32 generates a wavefront map, and computer 20 determines the aberrometer-based wavefront from the map.

Comparing Wavefronts. Computer 20 may compare the OCT-based wavefront and the aberrometer-based wavefront in any suitable manner. In certain embodiments, computer compares the wavefronts to see if they differ beyond a predefined tolerance. The predefined tolerance may be defined to accommodate known margins of error of measuring devices 28. For example, the predefined tolerance may be the largest of the known margins of error.

The wavefronts may be parameterized with the same parameters, and computer 20 may compare the wavefronts by comparing the values of the parameters. According to an example of operation, computer 20 parameterizes the OCT-based wavefront with parameters, where each parameter is assigned an OCT-based value that describes the OCT-based wavefront. Computer 20 parameterizes the aberrometer-based wavefront with the parameters, where each parameter is assigned an aberrometer-based value that describes the aberrometer-based wavefront. Computer 20 then compares the OCT-based values with the aberrometer-based values.

Generally, comparing more parameter values may increase the time needed to make the comparison. Accordingly, the number of parameters to compare may be selected in light of expected efficiency. In certain embodiments, computer 20 may perform a faster comparison that compares fewer parameter values in order to identify major deficiencies of the ocular model, which can be addressed before performing a more extensive (yet slower) comparison that compares more parameter values.

According to an example of a fast comparison, computer 20 may check the ocular model by generating a less detailed simulated wavefront. For example, computer 20 may determine a toric representation of interfaces 56 and then calculate sphere and cylinder parameters of a simulated wavefront through interfaces 56. The parameters of the simulated wavefront may be compared to the sphere and cylinder parameters of the aberrometer-based wavefront. A significant deviation may indicate a problem with, e.g., inaccurate axial length measurement, inadequate patient fixation, and/or inadequate device alignment or calibration. Computer 20 may send a notification identifying the problem or likely problems and/or a recommendation to redo the measurements with one or more measuring devices 28 (e.g., OCT device 30 and/or aberrometer 32) that could be responsible for the deviation.

According to another example of a faster comparison, computer 20 may check whether the parameters of the simulated wavefront conform to measurements from, e.g., topographer 34. For example, computer 20 may compare anterior corneal surface 58 of ocular model with surface 58 as measured by topographer 34. In the example, computer 20 determines a model-based anterior corneal surface from the ocular model and a topographer-based anterior corneal surface from topographer 34. Computer 20 checks the ocular model by comparing the model-based and topographer-based anterior corneal surfaces. A significant deviation may indicate a problem with, e.g., the tear film instability and/or inadequate device alignment or calibration. Computer 20 may send a notification identifying the problem or likely problems and/or a recommendation to redo the measurements with one or more measuring devices 28 (e.g., OCT device 30 and/or topographer 34) that could be responsible for the deviation.

According to an example of a more extensive comparison, computer 20 utilizes a wavefront map (e.g., a Zernike coefficient map) that includes wavefront parameters. In the example, computer 20 checks OCT-based values of an OCT-based wavefront with aberrometer-based values of an aberrometer-based wavefront. For example, the slopes of the aberrometer-based wavefront may be compared with the slopes of the rays exiting the eye according to the OCT-based model. Any suitable number of values that reconciles the OCT-based and aberrometer-based values (e.g., slopes) may be checked, e.g., 20 to 50, 50 to 100, or more than 100. The number of values may be adjusted according to desired completeness and/or efficiency. A significant deviation in the higher-order Zernike parametrization may indicate a problem with, e.g., tear film instability, inaccurate lens topography parameters, inadequate patient fixation, and/or inadequate device alignment or calibration. Computer 20 may send a notification identifying the problem or likely problens and/or a recommendation to redo the measurements with one or more measuring devices 28 (e.g., OCT device 30 and/or aberrometer 32) that could be responsible for the deviation.

Adjusting Parameter Values. If the OCT-based wavefront and the aberrometer-based wavefront differ beyond a predefined tolerance, computer 20 adjust one or more parameter values (such as a lens parameter value) of the OCT-based wavefront until a comparison of the wavefronts satisfies the predefined tolerance. Computer 20 adjusts the values by repeating the following: adjust values to yield an adjusted ocular model; determine an adjusted OCT-based wavefront according to the adjusted ocular model; and compare the adjusted OCT-based wavefront and the aberrometer-based wavefront to see if they satisfy the predefined tolerance.

Computer 20 may adjust the parameter values in any suitable manner. In certain embodiments, less certain values are adjusted before more certain values. Less certain values may include values that are not directly measured (e.g., lens refractive indices or cataract grading), values from less reliable measuring devices 28, or values given by softer constraints. More reliable values may include values supported by multiple measurements, values that are generally known in the field, or values given by harder constraints.

Performing Another Check. In certain embodiments, system 10 performs another check of the ocular model. In the embodiments, measuring devices 28 measure eye 12 from a different angle than was previously used to measure eye 12, and the measurements are compared. For example, measuring device 28 may first measure eye "on-axis", i.e., the optical axis of measuring device 28 is aligned with an axis (e.g., visual or optical) of eye 12. To check the ocular model, measuring device 28 may measure eye "off-axis", i.e., the axis of measuring device 28 is at an angle with the axis of eye. The angle may be, e.g., 0 to 10, and/or 10 to 20 degrees, such as approximately 3 degrees. Computer 20 uses the measurements at the different angle to generate new wavefronts to compare in order to check the ocular model.

For example, OCT device 30 directs OCT light towards the eye at the different angle and detects the OCT light reflected from the eye. Aberrometer 32 directs aberrometer light towards the eye at the different angle, detects the aberrometer light reflected from the eye, and generates an aberrometer-based wavefront. Computer 20 generates another ocular model of the eye according to the reflected OCT light and determines an OCT-based wavefront from the ocular model. Computer 20 then compares the wavefronts to check the ocular model.

Computer 20 stores the resulting ocular model in memory 24 and may output the model via interface 26. In certain embodiments, computer 20 uses the resulting ocular model to plan an ophthalmic surgery, e.g., a cataract or refractive surgery. For example, the model may be used to size accommodative intraocular lenses (IOLs) or to predict the post-operation position of an IOL.

Figure 6:
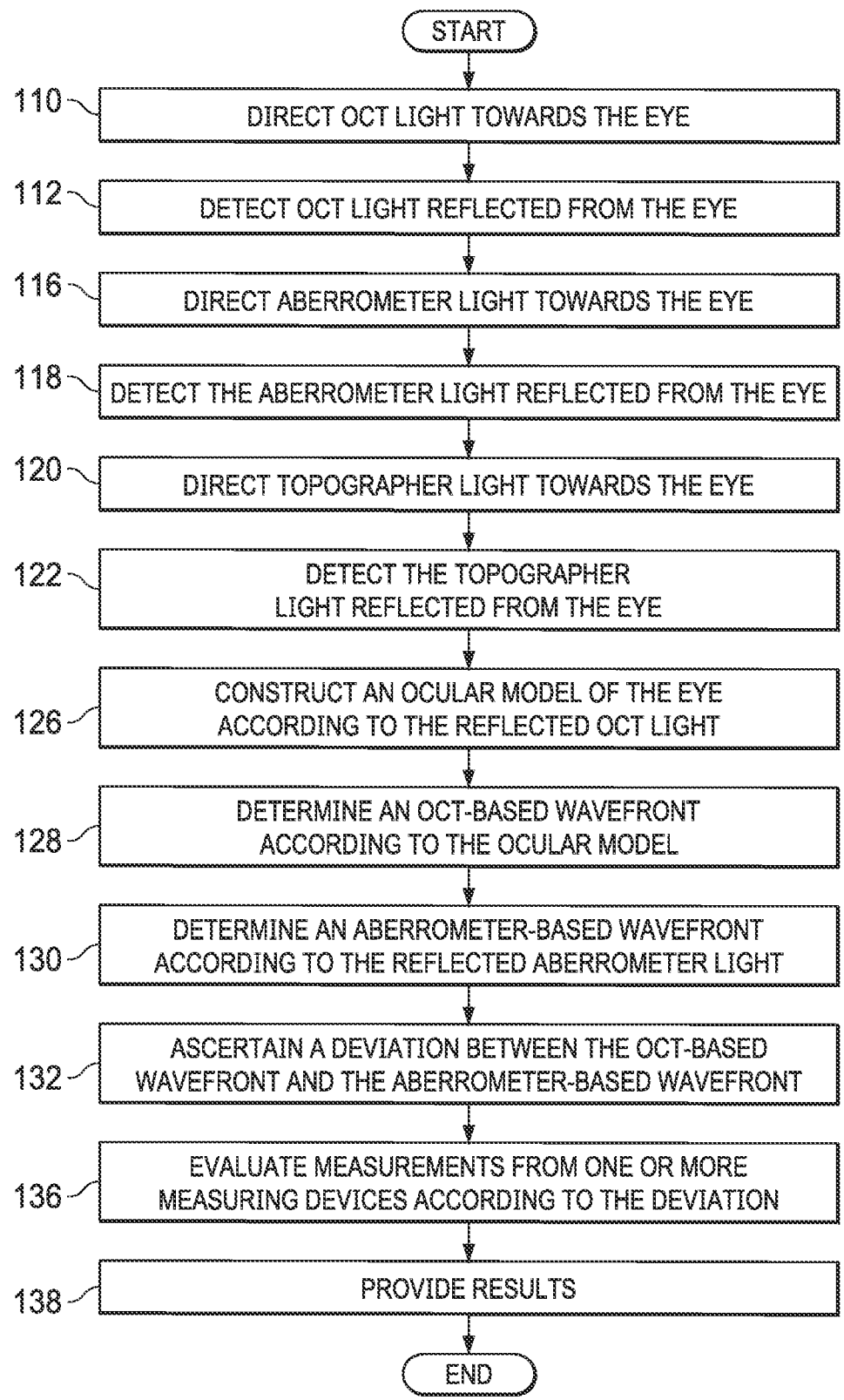
FIG. 6 illustrates an example of a method for evaluating measurements of an eye that may be performed by the system of FIG. 1, according to certain embodiments.

FIG. 6 illustrates an example of a method for evaluating measurements of an eye that may be performed by system 10 of FIG. 1, according to certain embodiments. In certain embodiments, computer 20 may perform steps of the method by sending instructions to the components of system 10.

The method starts at step 110, where OCT device 30 directs OCT light towards the eye, which reflects the light. OCT device 30 detects the reflected OCT light at step 112 to measure the eye. Aberrometer 32 directs aberrometer light towards the eye at step 116, and detects the aberrometer light reflected from the eye at step 118 to measure the eye. Topographer 34 directs topographer light towards the eye at step 120, and detects the aberrometer light reflected from the eye at step 122 to measure the eye.

Computer 20 constructs an ocular model of the eye according to the reflected OCT light at step 126. In certain embodiments, computer 20 applies a ray-tracing procedure to generate the ocular model. Certain embodiments may include variations in generating the ocular model. For example, computer 20 may construct the anterior corneal surface of the ocular model according to measurements from OCT device 30 and topographer 34. Computer 20 may determine an OCT-based anterior corneal surface from the ocular model, determine a topographer-based anterior corneal surface from the reflected topographer light, and check the ocular model by comparing the OCT-based and topographer-based anterior corneal surfaces. A deviation between the surfaces may indicate a problem such as an insufficient sampling, tear film instability, inadequate device alignment, and/or inadequate device calibration. If there is a deviation at this step, computer 20 may report the deviation such as at step 138.

Computer 20 determines an OCT-based wavefront according to the ocular model at step 128. Computer 20 may apply a ray-tracing process to calculate the OCT-based wavefront. Computer 20 determines an aberrometer-based wavefront according to the reflected aberrometer light at step 130. In certain embodiments, aberrometer 32 generates a wavefront map and provides the map to computer 20.

Computer 20 compares the OCT-based and aberrometer-based wavefronts and ascertains a deviation at step 132. Computer 20 may compare the wavefronts by parameterizing the wavefronts with parameter values and comparing the wavefront values. Computer 20 evaluates one or more measurements from one or more measuring devices according to the deviation at step 136. Computer 20 may evaluate measurements by identifying one or more problems related to the deviation. Related problems may be associated with a measurement condition or a measuring device. Examples of related problems associated with a measurement condition include a tear film instability and/or inadequate patient fixation. Examples of related problems associated with a measuring device include an inaccurate lens topography parameter, inadequate device alignment, and/or inadequate device calibration. Computer 20 may identify one or more measuring devices potentially responsible for the deviation.

In certain embodiments, the comparison at step 132 may inform computer 20 about the problems related to the deviation. For example, computer 20 may compare the wavefronts by: determining an OCT-based anterior corneal surface from the ocular model; determining a topographer-based anterior corneal surface from the reflected topographer light; and checking the ocular model by comparing the OCT-based and topographer-based anterior corneal surfaces. A deviation of the surfaces may indicate a problem such as an insufficient sampling, tear film instability, inadequate device alignment, and/or inadequate device calibration.

As another example, computer 20 may compare the wavefronts by: calculating OCT-based sphere and cylinder parameters of a simulated wavefront through the ocular model; calculating aberrometer-based sphere and cylinder parameters of the aberrometer-based wavefront; and comparing the OCT-based and aberrometer-based sphere and cylinder parameters. A deviation of the parameters may indicate a problem such as an inaccurate axial length measurement, inadequate patient fixation, inadequate device alignment, and/or inadequate device calibration.

As another example, computer 20 may compare the wavefronts by: determining one or more aberrometer-based values of the aberrometer-based wavefront; determining one or more OCT-based values of the ocular model; and comparing the aberrometer-based and OCT-based values. In some cases, the aberrometer-based values are aberrometer-based slopes of the aberrometer-based wavefront, and the OCT-based values are OCT-based slopes of rays exiting the ocular model. A deviation of the values may indicate a problem such as a tear film instability, inaccurate lens topography parameter, inadequate patient fixation, inadequate device alignment, and/or inadequate device calibration.

Computer 20 provides the results at step 138. Computer 20 may display the results and/or use the results in any suitable manner. For example, the results may be used to plan an ophthalmic surgery (e.g., cataract or refractive). The method then ends.

In certain embodiments, computer 20 may check the ocular model to improve the accuracy of the ocular model, which may yield improved detection and evaluation of measurements of the eye. For example, computer 20 may adjust one or more values assigned to parameters of the ocular model by repeating the following until an adjusted OCT-based wavefront and the aberrometer-based wavefront satisfies a predefined tolerance: adjusting the values to yield an adjusted ocular model; determining the adjusted OCT-based wavefront according to the adjusted ocular model; and comparing the adjusted OCT-based and aberrometer-based wavefronts to check if they satisfy the predefined tolerance.

As another example, system 10 may measure the eye at a different angle, and computer 20 may use the measurements to adjust the ocular model. In the example, the OCT device directs next OCT light towards the eye at an angle different from an angle of the OCT light, and detects the next OCT light reflected from the eye. The aberrometer directs next aberrometer light towards the eye at an angle different from an angle of the aberrometer light, and detects the next aberrometer light reflected from the eye. Computer 20 checks the ocular model by: generating a next ocular model of the eye according to the reflected next OCT light; generating a next aberrometer-based wavefront according to the reflected next aberrometer light; determining a next OCT-based wavefront according to the next ocular model; and comparing the next OCT-based and next aberrometer-based wavefronts.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic system for measuring an eye, comprising:
   a plurality of measuring devices, comprising:
      an optical coherence tomography (OCT) device configured to:
         direct OCT light towards the eye; and
         detect the OCT light reflected from the eye to measure the eye;
      an aberrometer configured to:
         direct aberrometer light towards the eye; and
         detect the aberrometer light reflected from the eye to measure the eye; and
   a computer configured to:
      generate an ocular model of the eye according to the reflected OCT light, the ocular model comprising a plurality of parameters for the eye, each parameter assigned a value;
      determine an OCT-based wavefront according to the ocular model;
      determine an aberrometer-based wavefront according to the reflected aberrometer light;
      ascertain a deviation between the OCT-based wavefront and the aberrometer-based wavefront; and
      evaluate one or more measurements from one or more of the plurality of measuring devices according to the deviation.

2. The ophthalmic system of claim 1, the computer configured to evaluate one or more measurements by:
identifying one or more problems related to the deviation.

3. The ophthalmic system of claim 2, the one or more related problems associated with a measurement condition or a measuring device.

4. The ophthalmic system of claim 2, the one or more related problems comprising a problem selected from a group consisting of a tear film instability, an inaccurate lens topography parameter, an inadequate patient fixation, an inadequate device alignment, and an inadequate device calibration.

5. The ophthalmic system of claim 1, computer configured to evaluate one or more measurements by:
identifying one or more measuring devices associated with the deviation.

6. The ophthalmic system of claim 1:
further comprising a topographer configured to:
direct topographer light towards the eye; and
detect the topographer light reflected from the eye; and
the computer configured to generate the ocular model of the eye by:
determining an OCT-based anterior corneal surface from the ocular model;
determining a topographer-based anterior corneal surface from the reflected topographer light; and
checking the ocular model by comparing the OCT-based anterior corneal surface and the topographer-based anterior corneal surface.

7. The ophthalmic system of claim 6, the computer configured to evaluate one or more measurements by:
identifying one or more related problems comprising a problem selected from a group consisting of an insufficient sampling, a tear film instability, an inadequate device alignment, and an inadequate device calibration.

8. The ophthalmic system of claim 1, the computer configured to ascertain the deviation between the OCT-based wavefront and the aberrometer-based wavefront by:
calculating OCT-based sphere and cylinder parameters of a simulated wavefront through the ocular model;
calculating aberrometer-based sphere and cylinder parameters of the aberrometer-based wavefront; and
comparing the OCT-based sphere and cylinder parameters and the aberrometer-based sphere and cylinder parameters.

9. The ophthalmic system of claim 8, the computer configured to evaluate one or more measurements by:
identifying one or more related problems comprising a problem selected from a group consisting of an inaccurate axial length measurement, an inadequate patient fixation, an inadequate device alignment, and an inadequate device calibration.

10. The ophthalmic system of claim 1, the computer configured to ascertain the deviation between the OCT-based wavefront and the aberrometer-based wavefront by:
determining one or more aberrometer-based values of the aberrometer-based wavefront;
determining one or more OCT-based values of the ocular model; and
comparing the one or more aberrometer-based values and the OCT-based values.

11. The ophthalmic system of claim 10:
the one or more aberrometer-based values comprising one or more aberrometer-based slopes of the aberrometer-based wavefront; and
the one or more OCT-based values comprising one or more OCT-based slopes of one or more rays exiting the ocular model.

12. The ophthalmic system of claim 1, wherein the computer is further configured to adjust one or more values assigned to one or more of the parameters by repeating the following until an adjusted OCT-based wavefront and the aberrometer-based wavefront satisfies a predefined tolerance:
adjusting the one or more values to yield an adjusted ocular model;
determining the adjusted OCT-based wavefront according to the adjusted ocular model; and
comparing the adjusted OCT-based wavefront and the aberrometer-based wavefront to check if they satisfy the predefined tolerance.

13. The ophthalmic system of claim 1:
the OCT device further configured to check the ocular model by:
directing next OCT light towards the eye at an angle different from an angle of the OCT light; and
detecting the next OCT light reflected from the eye; and
the aberrometer further configured to check the ocular model by:
directing next aberrometer light towards the eye at an angle different from an angle of the aberrometer light; and
detecting the next aberrometer light reflected from the eye; and
the computer further configured to check the ocular model by:
generating a next ocular model of the eye according to the reflected next OCT light;
generating a next aberrometer-based wavefront according to the reflected next aberrometer light;
determining a next OCT-based wavefront according to the next ocular model; and
comparing the next OCT-based wavefront and the next aberrometer-based wavefront.

14. An ophthalmic system for measuring an eye, comprising:
a plurality of measuring devices, comprising:
an optical coherence tomography (OCT) device configured to:
direct OCT light towards the eye; and
detect the OCT light reflected from the eye;
a topographer configured to:
direct topographer light towards the eye; and
detect the topographer light reflected from the eye; and
a computer configured to:
determine an OCT-based anterior corneal surface from the reflected OCT light;
determine a topographer-based anterior corneal surface from the reflected topographer light;
ascertain a deviation between the OCT-based anterior corneal surface and topographer-based anterior corneal surface; and
evaluate the OCT-based anterior corneal surface and the topographer-based anterior corneal surface according to the deviation.

15. The ophthalmic system of claim 14, the computer configured to evaluate the OCT-based anterior corneal surface and the topographer-based anterior corneal surface by:
identifying one or more problems related to the deviation.

16. The ophthalmic system of claim 15, the one or more related problems associated with a measurement condition or a measuring device.

17. The ophthalmic system of claim 15, the one or more related problems comprising one or more problems selected from the group consisting of an insufficient sampling, an inadequate device alignment, and an inadequate device calibration.

18. The ophthalmic system of claim 14, the computer configured to evaluate the OCT-based anterior corneal surface and the topographer-based anterior corneal surface by:
identifying one or more measuring devices associated with the deviation.

19. The ophthalmic system of claim 14:
the plurality of measuring devices further comprising an aberrometer configured to:
direct aberrometer light towards the eye; and
detect the aberrometer light reflected from the eye; and
the computer further configured to:
generate an ocular model of the eye according to the reflected OCT light, the ocular model comprising a plurality of parameters for the eye, each parameter assigned a value;
determine an OCT-based wavefront according to the ocular model;
determine an aberrometer-based wavefront according to the reflected aberrometer light;
compare the OCT-based wavefront and the aberrometer-based wavefront; and
evaluate one or more measurements from one or more of the plurality of measuring devices according to the comparison.

20. An ophthalmic system for measuring an eye, comprising:
a plurality of measuring devices, comprising:
an optical coherence tomography (OCT) device configured to:
direct OCT light towards the eye; and
detect the OCT light reflected from the eye to measure the eye;
an aberrometer configured to:
direct aberrometer light towards the eye; and
detect the aberrometer light reflected from the eye to measure the eye;
a topographer configured to:
direct topographer light towards the eye; and
detect the topographer light reflected from the eye; and
a computer configured to:
generate an ocular model of the eye according to the reflected OCT light, the ocular model comprising a plurality of parameters for the eye, each parameter assigned a value, the ocular model generated by: determining an OCT-based anterior corneal surface from the ocular model, determining a topographer-based anterior corneal surface from the reflected topographer light, and checking the ocular model by comparing the OCT-based anterior corneal surface and the topographer-based anterior corneal surface;
determine an OCT-based wavefront according to the ocular model;
determine an aberrometer-based wavefront according to the reflected aberrometer light;
ascertain a deviation between the OCT-based wavefront and the aberrometer-based wavefront, the deviation between the OCT-based wavefront and the aberrometer-based wavefront ascertained by:
calculating OCT-based sphere and cylinder parameters of a simulated wavefront through the ocular model, calculating aberrometer-based sphere and cylinder parameters of the aberrometer-based wavefront, and comparing the OCT-based sphere and cylinder parameters and the aberrometer-based sphere and cylinder parameters; and
determining one or more aberrometer-based values of the aberrometer-based wavefront, determining one or more OCT-based values of the ocular model, and comparing the one or more aberrometer-based values and the OCT-based values, wherein the one or more aberrometer-based values comprise one or more aberrometer-based slopes of the aberrometer-based wavefront, and the one or more OCT-based values comprise one or more OCT-based slopes of one or more rays exiting the ocular model; and
evaluate one or more measurements from one or more of the plurality of measuring devices according to the deviation by:
identifying one or more problems related to the deviation and associated with a measurement condition or a measuring device, the one or more related problems comprising a problem selected from a group consisting of an inaccurate axial length measurement, an insufficient sampling, a tear film instability, an inaccurate lens topography parameter, an inadequate patient fixation, an inadequate device alignment, and an inadequate device calibration; and
identifying one or more measuring devices associated with the deviation; and
adjust one or more values assigned to one or more of the parameters by repeating the following until an adjusted OCT-based wavefront and the aberrometer-based wavefront satisfies a predefined tolerance: adjusting the one or more values to yield an adjusted ocular model, determining the adjusted OCT-based wavefront according to the adjusted ocular model, and comparing the adjusted OCT-based wavefront and the aberrometer-based wavefront to check if they satisfy the predefined tolerance;
the OCT device further configured to check the ocular model by: directing next OCT light towards the eye at an angle different from an angle of the OCT light, and detecting the next OCT light reflected from the eye;
the aberrometer further configured to check the ocular model by: directing next aberrometer light towards the eye at an angle different from an angle of the aberrometer light, and detecting the next aberrometer light reflected from the eye; and
the computer further configured to check the ocular model by: generating a next ocular model of the eye according to the reflected next OCT light, generating a next aberrometer-based wavefront according to the reflected next aberrometer light, determining a next OCT-based wavefront according to the next ocular model, and comparing the next OCT-based wavefront and the next aberrometer-based wavefront.

* * * * *